(12) United States Patent
Zabotkin et al.

(10) Patent No.: US 12,727,866 B2
(45) Date of Patent: Sep. 8, 2026

(54) SURGICAL TOOL END EFFECTORS WITH REPLACEABLE BLADES

(71) Applicant: Cilag GmbH International, Zug (CH)

(72) Inventors: Konstantin Zabotkin, Mason, OH (US); Austin Wise, Cincinnati, OH (US); Pavel Shalakov, Blue Ash, OH (US)

(73) Assignee: Cilag GmbH International, Zug (CH)

( * ) Notice: Subject to any disclaimer, the term of this patent is extended or adjusted under 35 U.S.C. 154(b) by 400 days.

(21) Appl. No.: 18/366,020

(22) Filed: Aug. 7, 2023

(65) Prior Publication Data

US 2025/0049461 A1 Feb. 13, 2025

(51) Int. Cl.
*A61B 17/00* (2006.01)
*A61B 17/295* (2006.01)
*A61B 17/29* (2006.01)

(52) U.S. Cl.
CPC ............ *A61B 17/00* (2013.01); *A61B 17/295* (2013.01); *A61B 2017/00477* (2013.01); *A61B 2017/00526* (2013.01); *A61B 2017/2908* (2013.01)

(58) Field of Classification Search
CPC ....... A61B 17/28; A61B 17/29; A61B 17/295; A61B 2017/0047; A61B 2017/2908; A61B 34/30; A61B 34/71; A61B 2034/305; A61B 17/00
See application file for complete search history.

(56) References Cited

U.S. PATENT DOCUMENTS

2013/0158542 A1 6/2013 Manzo et al.
2019/0105099 A1* 4/2019 Murrell .................. A61B 34/71
2024/0398467 A1* 12/2024 Hibner ............... A61B 18/1445

FOREIGN PATENT DOCUMENTS

WO 2022269421 A1 12/2022

OTHER PUBLICATIONS

Written Opinion and International Search Report from corresponding PCT Application No. PCT/IB2024/057557 mailed Nov. 27, 2024.

* cited by examiner

*Primary Examiner* — Sarah A Long
(74) *Attorney, Agent, or Firm* — Vorys, Sater, Seymour and Pease LLP

(57) ABSTRACT

A method of replacing blades of an end effector of a surgical tool includes moving the end effector distally from an assembled state, where the end effector is rotatably mounted to a clevis, to an extended state, where an axle is dislodged from open-ended slots defined in opposing arms of the clevis. The end effector includes opposing first and second blades mounted to first and second blade holders rotatably mounted to the axle. The blade holders are separable from the blades in opposing lateral directions, and a new blade set comprising new blades and a new axle are then mountable to the holders, and the end effector is moved proximally and back to the assembled state by receiving the new axle within the open-ended slots.

9 Claims, 11 Drawing Sheets

1200
210
212
404a
706
708
710
702
1204
1206

SURGICAL TOOL END EFFECTORS WITH REPLACEABLE BLADES

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

Some end effectors include high-wear components that can mechanically or physically degrade over time and thereby limit the useful life of the end effector. One example of high-wear components is the blades of surgical scissors, which can dull over time, and thereby adversely affect the efficiency of the end effector. What is needed is a method and system of more easily replacing the blades of an end effector, which can provide a user (e.g., a surgeon, a nurse, etc.) with a new set of blades for every new use of the surgical tool.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to methods and systems of replacing blades of end effector surgical scissors.

The methods and systems for replacing end effector blades discussed herein include moving an end effector distally from an assembled state, where the end effector is rotatably mounted to a clevis, to an extended state, where an axle is dislodged from open-ended slots defined in opposing arms of the clevis. The end effector includes opposing first and second blades mounted to first and second blade holders rotatably mounted to the axle. The blade holders are separable from the blades in opposing lateral directions, and a new blade set comprising new blades and a new axle are then mountable to the holders, and the end effector is moved proximally and back to the assembled state by receiving the new axle within the open-ended slots.

Figure 1:
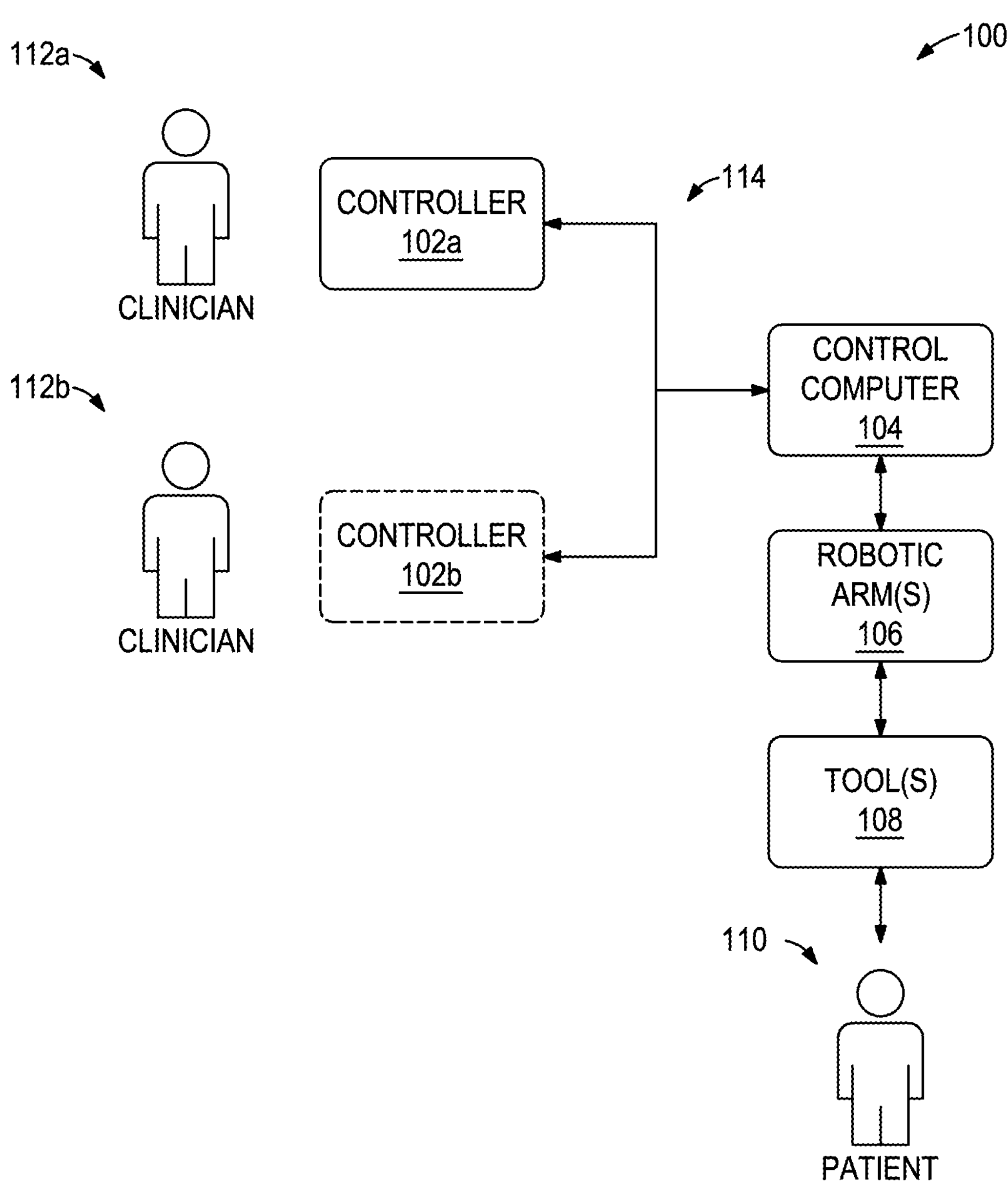
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
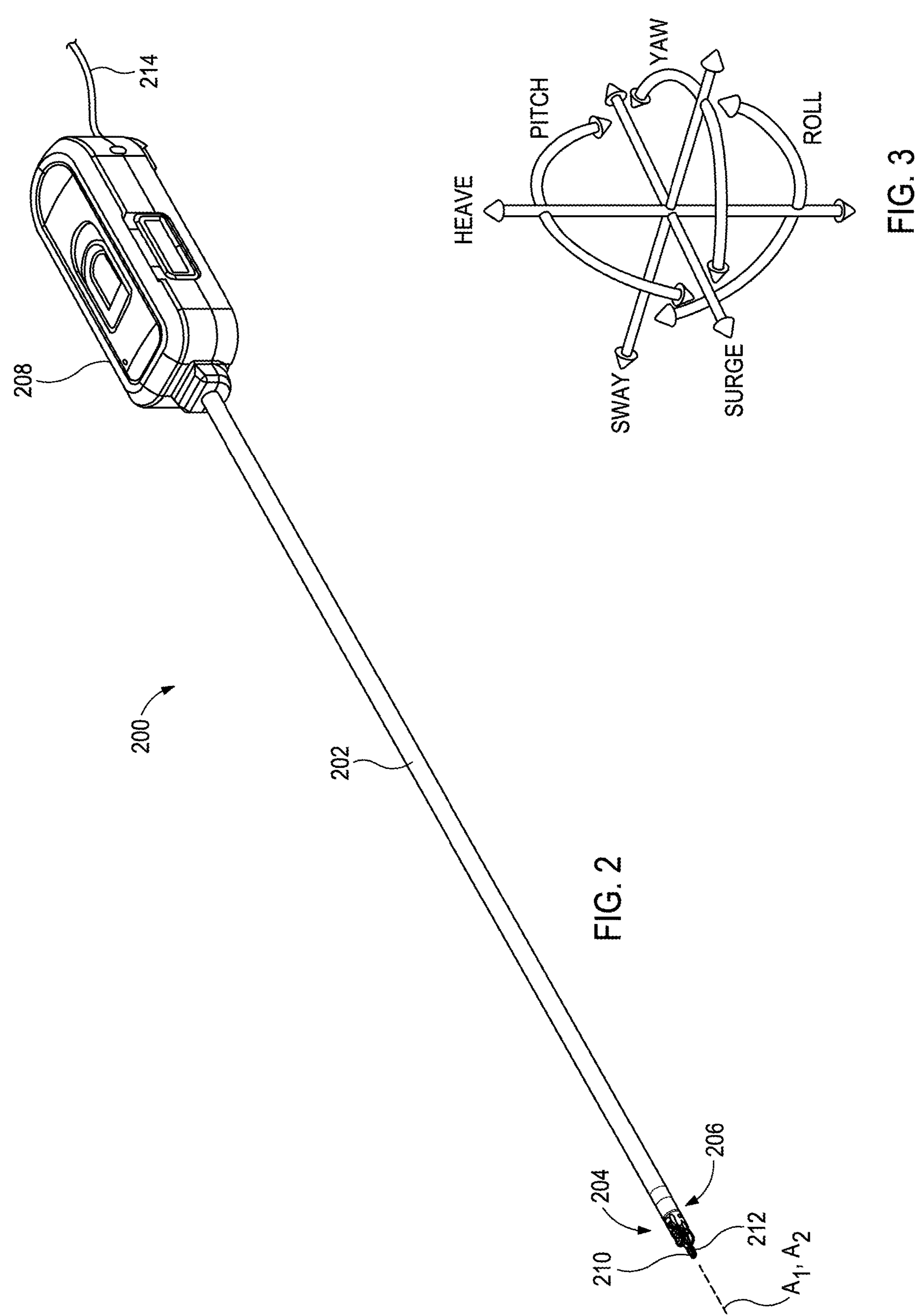
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises surgical scissors that includes opposing first (upper) and second (lower) blades 210, 212 configured to move (articulate) between open and closed positions. As will be appreciated, however, the blades 210, 212 may alternatively comprise opposing jaws that form part of other types of end effectors such as, but not limited to, a needle driver, a clip applier, a tissue grasper, a vessel sealer, a combination tissue grasper and vessel sealer, a babcock including a pair of opposed grasping jaws, bipolar jaws (e.g., bipolar Maryland grasper, forceps, a fenestrated grasper, etc.), etc. One or both of the blades 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Similar to most surgical tools, the surgical tool 200 includes various high-wear components referred to herein as "consumables" that, over time, can mechanically or physically degrade and thereby limit the useful life of the surgical tool 200. Consequently, the surgical tool 200 may be designed to be used for only a predetermined number of procedures. Once the predetermined number of procedures is reached, the operator (e.g., a nurse, a doctor, etc.) may be unable to continue using the surgical tool 200. In such cases, the surgical tool 200 would conventionally be discarded, which can have an adverse impact on the environment.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator that supplies energy, such as electrical energy (e.g., radio frequency energy), ultrasonic energy, microwave energy, heat energy, or any combination thereof, to the surgical tool 200 and, more particularly, to the end effector 204. Accordingly, the generator may comprise a radio frequency (RF) source, an ultrasonic source, a direct current source, and/or any other suitable type of electrical energy source that may be activated independently or simultaneously.

Figure 4:
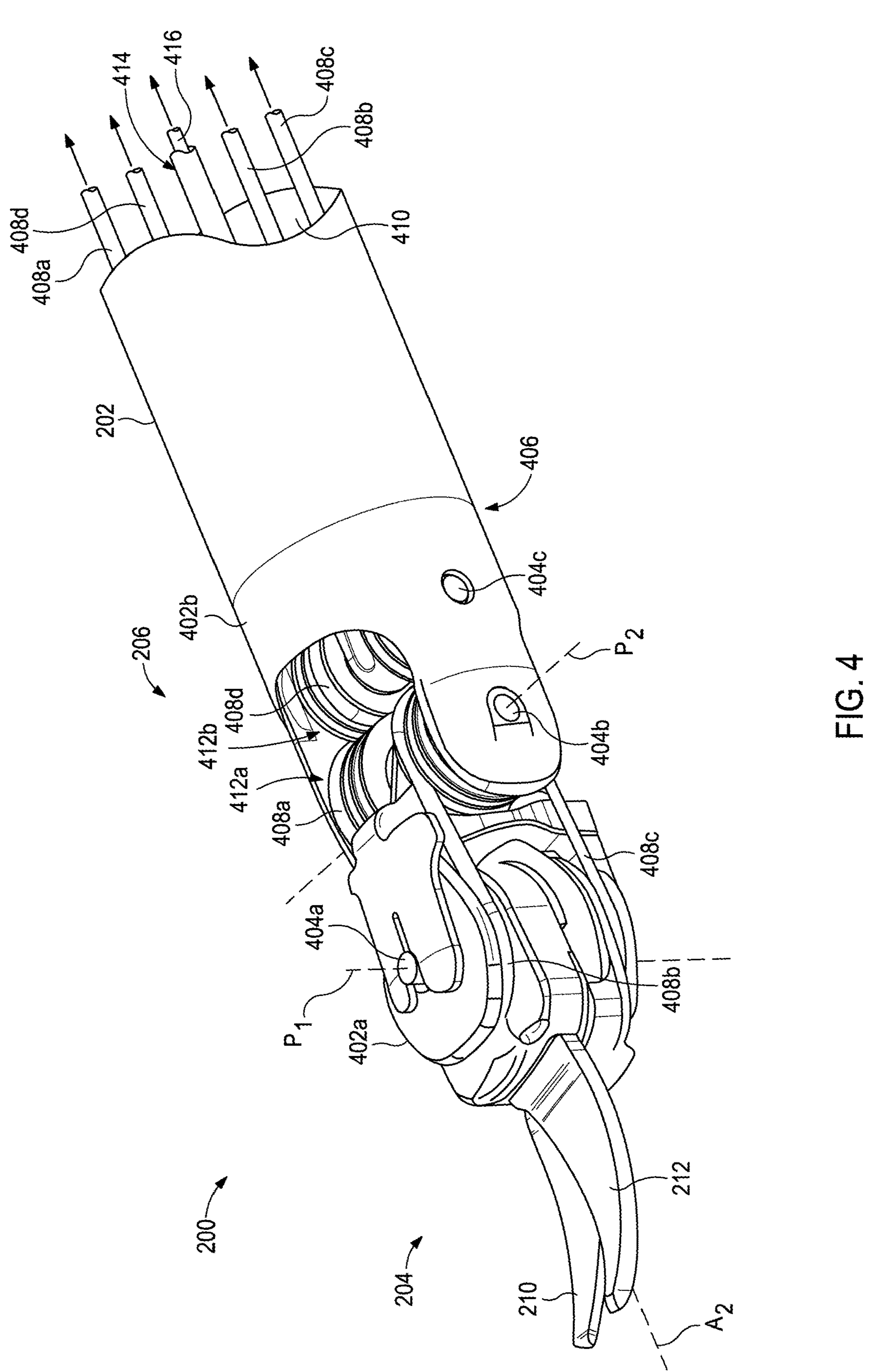
FIG. 4 is an enlarged isometric view of the distal end of the surgical tool of FIG. 2.

FIG. 4 is an enlarged isometric view of the distal end of the surgical tool 200, according to one or more embodiments. More specifically, FIG. 4 depicts enlarged views of the end effector 204 and the wrist 206, with the end effector 204 in the unarticulated position. The wrist 206 operatively couples the end effector 204 to the shaft 202. To accomplish this, the wrist 206 includes a distal clevis 402*a* and a proximal clevis 402*b*. The end effector 204 (i.e., the blades 210, 212) is rotatably mounted to the distal clevis 402*a* at a first axle 404*a*, the distal clevis 402*a* is rotatably mounted to the proximal clevis 402*b* at a second axle 404*b*, and the proximal clevis 402*b* is coupled to a distal end 406 of the shaft 202.

The wrist 206 provides a first pivot axis $P_1$ that extends through the first axle 404*a* and a second pivot axis $P_2$ that extends through the second axle 404*b*. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. In the illustrated embodiment, the blades 210, 212 are mounted at the first pivot axis $P_1$, thereby allowing the blades 210, 212 to pivot relative to each other to open and close the end effector 204 or alternatively pivot in tandem to articulate the orientation of the end effector 204.

A plurality of drive cables, shown as drive cables 408*a*, 408*b*, 408*c*, and 408*d*, extend longitudinally within a lumen 410 defined by the shaft 202 and pass through the wrist 206 to be operatively coupled to the end effector 204. While four drive cables 408*a-d* are depicted in FIG. 4, more or less than four drive cables 408*a-d* may be included, without departing from the scope of the disclosure.

The drive cables 408*a-d* form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 706*a-d* can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 408*a-d* are depicted in FIG. 4, more or less than four may be employed, without departing from the scope of the disclosure.

The drive cables 408*a-d* extend proximally from the end effector 204 to the drive housing 208 (FIG. 2) where they are operatively coupled to various actuation mechanisms or devices housed (contained) therein to facilitate longitudinal movement (translation) of the drive cables 408*a-d* within the lumen 410. Selective actuation of all or a portion of the drive cables 408*a-d* causes the end effector 204 (e.g., one or both of the blades 210, 212) to articulate (pivot) relative to the shaft 202. More specifically, selective actuation causes a corresponding drive cable 408*a-d* to translate longitudinally within the lumen 410 and thereby cause pivoting movement of the end effector 204. One or more drive cables 408*a-d*, for example, may translate longitudinally to cause the end effector 204 to articulate (e.g., both of the blades 210, 212 angled in a same direction), to cause the end effector 204 to open (e.g., one or both of the blades 210, 212 move away from the other), or to cause the end effector 204 to close (e.g., one or both of the blades 210, 212 move toward the other).

Moving the drive cables 408*a-d* can be accomplished in a variety of ways, such as by triggering an associated actuator or mechanism operatively coupled to or housed within the drive housing 208 (FIG. 2). Moving a given drive cable 408*a-d* constitutes applying tension (i.e., pull force) to the given drive cable 408*a-d* in a proximal direction, which causes the given drive cable 408*a-d* to translate and thereby cause the end effector 204 to move (articulate) relative to the shaft 202.

The wrist 206 includes a first plurality of pulleys 412*a* and a second plurality of pulleys 412*b*, each configured to interact with and redirect the drive cables 408*a-d* for engagement with the end effector 204. The first plurality of pulleys 412*a* is mounted to the proximal clevis 402*b* at the second axle 404*b* and the second plurality of pulleys 412*b* is also mounted to the proximal clevis 402*b* but at a third axle 404*c* located proximal to the second axle 404*b*. The first and second pluralities of pulleys 412*a,b* cooperatively redirect the drive cables 408*a-d* through an "S" shaped pathway before the drive cables 408*a-d* are operatively coupled to the end effector 204.

In at least one embodiment, one pair of drive cables 408*a-d* is operatively coupled to each blade 210, 212 and configured to "antagonistically" operate the corresponding blade 210, 212. In the illustrated embodiment, for example, the first and second drive cables 408*a,b* are coupled to (terminate at) the first blade 210, and the third and fourth drive cables 408*c,d* are coupled to (terminate at) the second blade 212. Actuation of the first drive cable 408*a* acts on and pivots the first blade 210 about the first pivot axis $P_1$ toward the closed position. In contrast, actuation of the second drive cable 408*b* acts on and pivots the first blade 210 about the first pivot axis $P_1$ toward the open position. Similarly, actuation of the third drive cable 408*c* pivots the second blade 212 about the first pivot axis $P_1$ toward the closed position, while actuation of the fourth drive cable 408*d* pivots the second blade 212 about the first pivot axis $P_1$ toward the open position.

Accordingly, the drive cables 408*a-d* may be characterized or otherwise referred to as "antagonistic" cables that cooperatively (yet antagonistically) operate to cause relative or tandem movement of the first and second blades 210, 212. When the first drive cable 408*a* is actuated (moved), the second drive cable 408*b* naturally follows since it is also coupled to the first blade 210, and vice versa. Similarly, when the third drive cable 408*c* is actuated, the fourth drive cable 408*d* naturally follows since it is also coupled to the second blade 210, and vice versa.

The surgical tool 200 may also include an electrical conductor 414 that supplies electrical energy to the end effector 204, thereby converting the surgical tool 200 into an "electrosurgical instrument". In other embodiments, however, the electrical conductor 414 may be omitted, and the end effector 204 may operate merely as surgical scissors. In embodiments where the end effector 204 comprises an electrosurgical instrument, however, the electrical conductor 414 extends longitudinally within the lumen 410 and passes through the wrist 206 to be operatively (and electrically) coupled to the end effector 204. In some embodiments, the electrical conductor 414 and the power cable 214 (FIG. 2) may comprise the same structure. In other embodiments, however, the electrical conductor 414 may be electrically coupled to the power cable 214. In yet other embodiments, the electrical conductor 414 may extend to the drive housing 208 (FIG. 2) where it is electrically coupled to an internal power source, such as batteries or fuel cells.

The electrical conductor 414 may include a supply conductor 416 encapsulated by an insulating cover (e.g., an insulated wire). In the illustrated embodiment, the end effector 204 is configured for monopolar operation. Accordingly, electrical energy is transmitted by the supply conductor 416 to the end effector 204, which acts as an active (or source) electrode. In at least one embodiment, the electrical energy may comprise radio frequency ("RF") energy exhibiting a frequency between about 100 kHz and 1 MHZ. Low frequency RF energy causes ionic agitation or friction, in effect resistive heating, thereby increasing the temperature of target tissue. Accordingly, electrical energy supplied to the end effector 204 is converted to heat and transferred to adjacent tissue to cut, cauterize, and/or coagulate the tissue (dependent upon the localized heating of the tissue), and thus may be particularly useful for sealing blood vessels or diffusing bleeding. Electrical energy is then returned from the tissue through a return electrode, which typically comprises a grounding pad separately located on a patient's body.

Figure 5B:
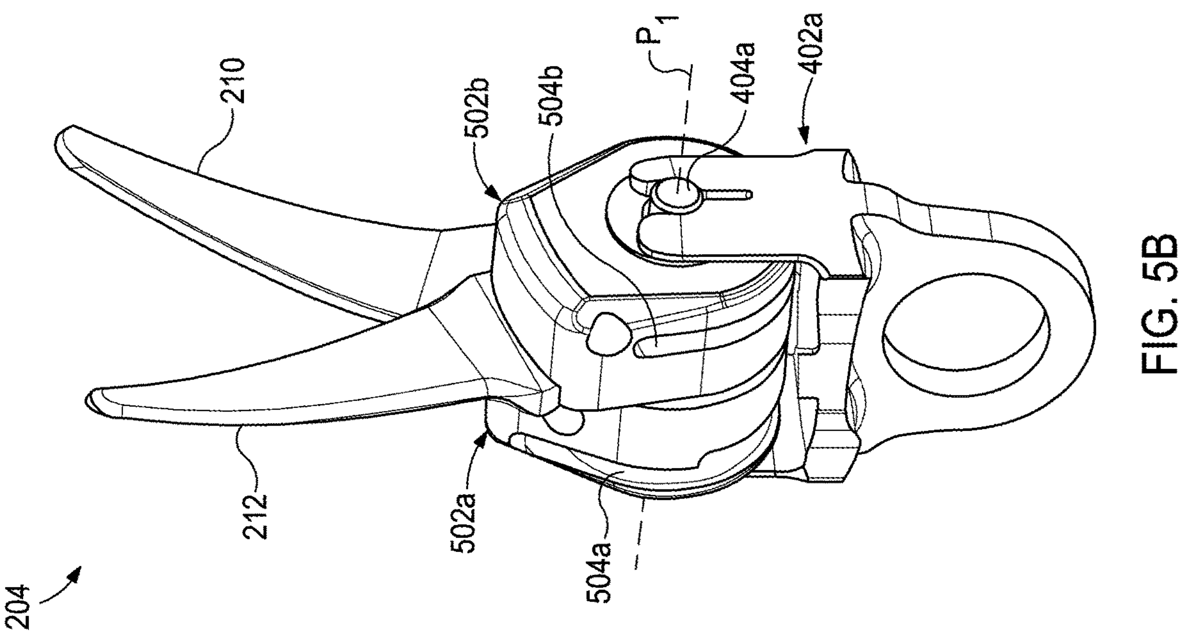
FIGS. 5A and 5B are enlarged left and right isometric views, respectively, of the end effector of FIG. 4, according to one or more embodiments.
Figure 5A:
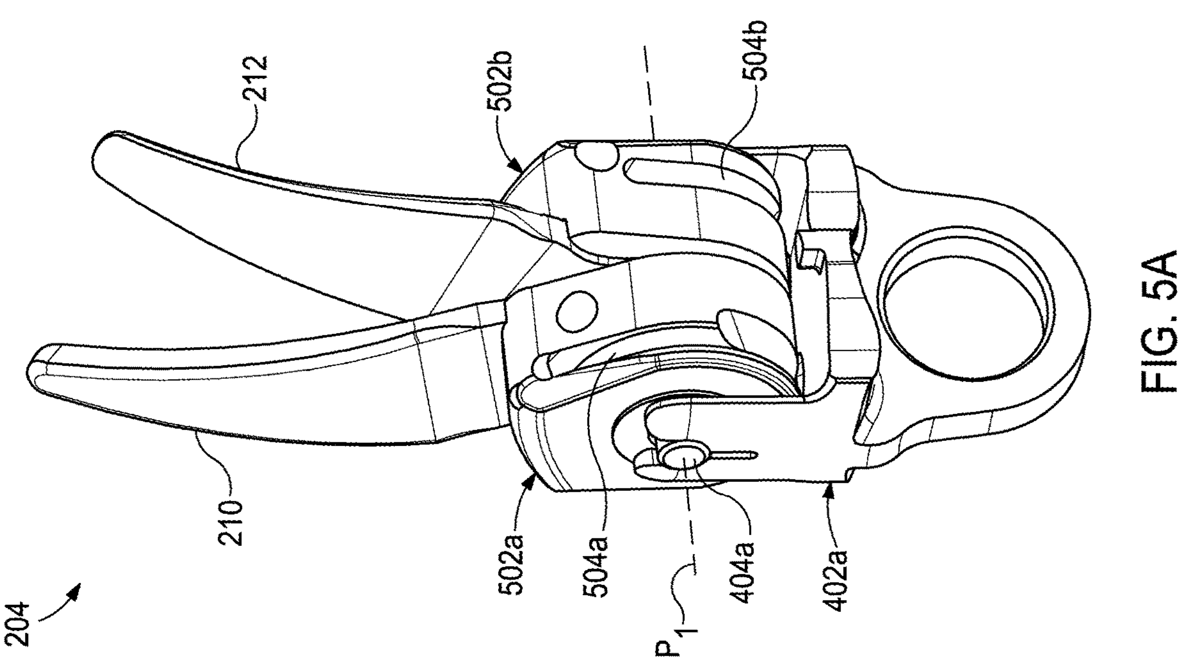

FIGS. 5A and 5B are enlarged left and right isometric views, respectively, of the end effector 204 of FIG. 4, according to one or more embodiments. As mentioned above, the end effector 204 includes the first and second blades 210, 212 rotatably mounted to the distal clevis 402*a* at the first axle 404*a*. The drive cables 408*a-d* of FIG. 4 are omitted to enable better viewing of the component parts of the end effector 204.

As illustrated, the end effector 204 further includes first and second blade holders 502*a* and 502*b* rotatably mounted to the first axle 404*a* and laterally offset from each other. The first blade holder 502*a* is configured to receive and seat the first blade 210 such that movement (rotation) of the first blade holder 502*a* about the first pivot axis $P_1$ correspondingly moves (rotates) the first blade 210. The first blade holder 502*a* may also provide and otherwise define a first pulley 504*a* configured to receive and seat one or more drive cables, such as the third and fourth drive cables 408*c,d* of FIG. 4, to effect such movement (rotation). The second blade holder 502*b* is configured to receive and seat the second blade 212 such that movement (rotation) of the second blade holder 502*b* about the first pivot axis $P_1$ correspondingly moves (rotates) the second blade 212. The second blade holder 502*b* may also provide and otherwise define a second pulley 504*b* configured to receive and seat one or more drive cables, such as the first and second drive cables 408*a,b* of FIG. 4, to effect such movement (rotation).

As used herein, the term "blade holder" is intended to apply to a variety of types of end effectors having opposing blades or jaws that are movable relative to one another. In the illustrated embodiment, the blades 210, 212 comprise opposing scissor blades of a surgical scissors end effector. In other embodiments, however, the blades 210, 212 may alternatively comprise opposing jaws used in a grasper end effector, or the like, and the term "jaw holder" similarly applies, without departing from the scope of the disclosure. Moreover, the term "holder" in "blade holder" may be replaced with "mount," "drive member," or "actuation member."

In some embodiments, the first and second blade holders 502*a,b* may be made of an electrically insulating or nonconductive material. Suitable non-conductive materials include, but are not limited to, a ceramic (e.g., zirconia, alumina, aluminum nitride, a silicate, silicon nitride, etc.), high temperature and high strength plastics, a thermoplastic or thermosetting polymer (e.g., polyether ether ketone, ULTEM™, VESPEL®, a polyphenylsulfone, a polysulfone, RADEL®, a polyamide-imide, a polyimide, an epoxy, etc.), a composite material (e.g., fiberglass), hard rubber (e.g., ebonite), or any combination thereof. Alternatively, the proximal region of the blades 210, 212 may be coated in a nonconductive material (e.g., ceramic) to isolate the proximal regions of the blades 210, 212 from the blade holders 502*a,b* that isolated the blades 210, 212 from the rest of the wrist components, thus allowing these wrist components to be constructed out of a traditional conductive material such as stainless steel.

In some embodiments, the first and second blade holders 502*a,b* may each comprise a monolithic structure made of a common (singular) material. In other embodiments, however, one or both of the blade holders 502*a,b* may comprise two or more portions joined together to form the blade holder 502*a,b*. In such embodiments, for example, a first portion of the blade holder 502*a,b* may be configured to receive the blade 210, 212 and the second portion may provide the corresponding pulley 504*a,b*. Moreover, in such embodiments, the first and second portions may be made of the same or dissimilar materials. The first portion, for example, may be made of a non-conductive material (e.g., ceramic or a polymer) and the second portion may be made of a dissimilar non-conductive material or alternatively a conductive material. In other embodiments, the first and second portions may be made of dissimilar non-conductive materials. In such embodiments, the first portion may be made of ceramic, and the second portion may be made of a plastic overmolded onto the first portion and otherwise coupled thereto.

Figure 6B:
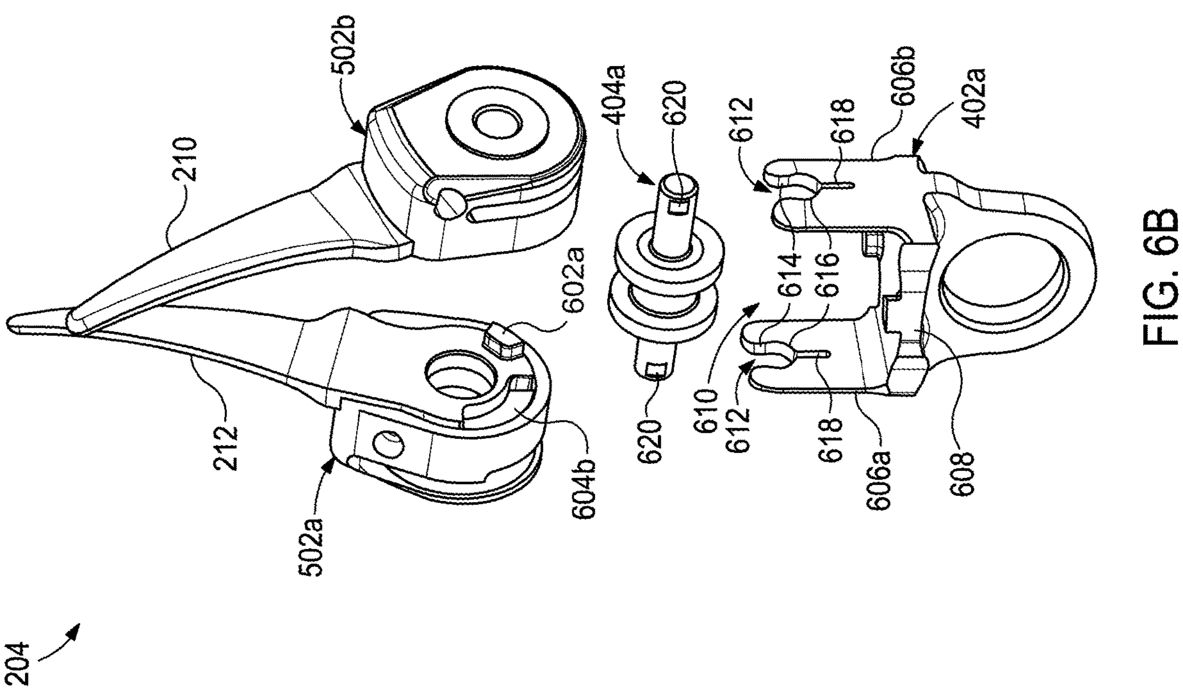
FIGS. 6A and 6B are exploded left and right isometric views, respectively, of the end effector of FIG. 4, according to one or more embodiments.
Figure 6A:
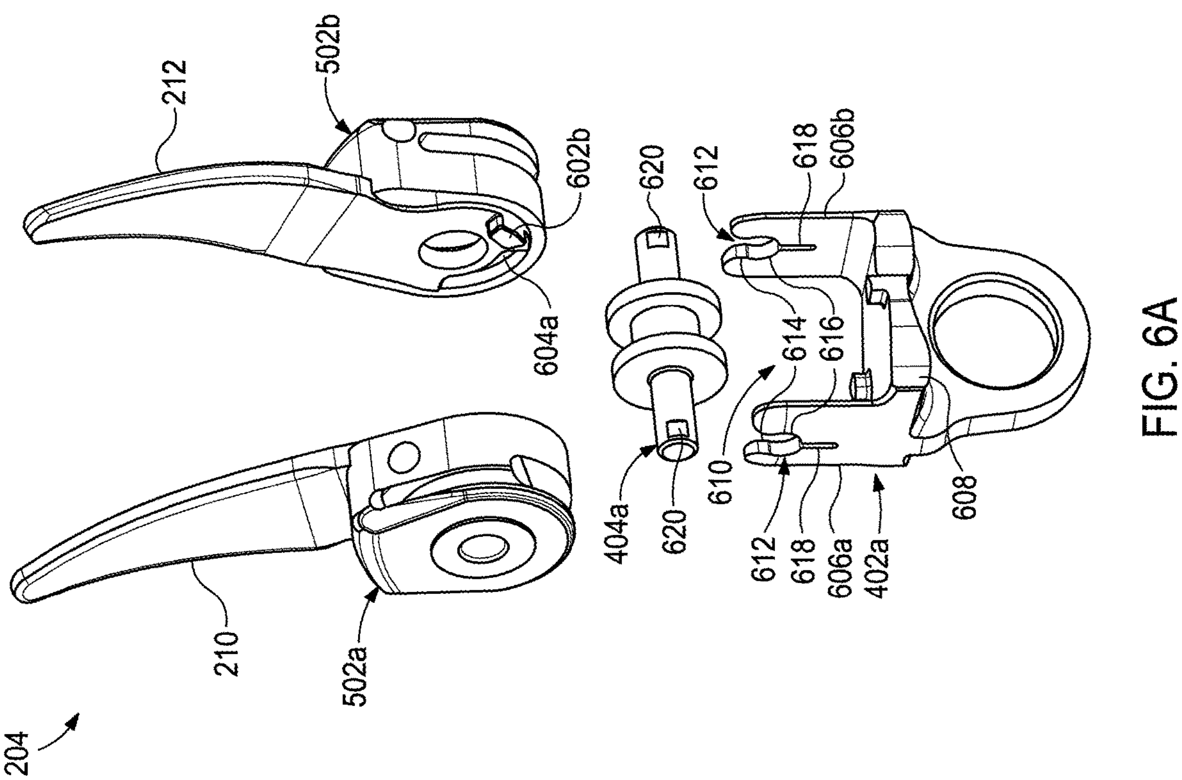

FIGS. 6A and 6B are exploded left and right isometric views, respectively, of the end effector 204 of FIGS. 5A-5B, according to one or more embodiments. More specifically, FIGS. 6A-6B show the blades 210, 212 and corresponding blade holders 502*a,b* removed and exploded away from the first axle 404*a*, and the first axle 404*a* exploded away from the distal clevis 402*a*.

As illustrated, the first blade 210 includes a first projection 602*a* (FIG. 6B) configured to be received within a first arcuate slot 604*a* (FIG. 6A) defined in the second blade 212 when the blades 210, 212 and corresponding blade holders 502*a,b* are mounted to the first axle 404*a*. Similarly, the second blade 212 includes a second projection 602*b* (FIG. 6A) configured to be received within a second arcuate slot 604*b* (FIG. 6B) defined in the first blade 210 when the blades 210, 212 and corresponding blade holders 502*a,b* are mounted to the first axle 404*a*. Receiving the projections 602*a,b* into the corresponding arcuate slots 604*b,a*, respectively, helps prevent the blades 210, 212 from over-rotating (in both angular directions) during operation.

The distal clevis 402*a* provides opposing first and second arms 606*a* and 606*b* laterally offset from each other and extending distally from a main body 608. A space or gap 610 is formed between the arms 606*a,b* and is sized to receive the combination blades 210, 212 and blade holders 502*a,b* as mounted to the first axle 404*a*. Each arm 606*a,b* provides and otherwise defines an open-ended slot 612 open in the distal direction, and each slot 612 is configured to receive and seat an opposing end of the first axle 404*a*. In some embodiments, as illustrated, each slot 612 may define a minimized section 614 that leads into an enlarged section 616. The minimized section 614 provides a smaller gap (space) as compared to the enlarged section 616 and, as a result, the first axle 404*a* may need to be forced through the minimized section 614 before reaching the enlarged section 616 and otherwise to be disassembled from the distal clevis 402*a*. This may prove advantageous in helping to prevent the first axle 404*a* from inadvertently escaping from the slots 612 during operation. Accordingly, the open-ended slots 612 may be configured to provide a snap fit or interference fit that allows the first axle 404*a* to be dislodged distally upon application of force.

In some embodiments, a longitudinal slit 618 may be defined in each arm 606*a,b* extending contiguous with and away from the corresponding slot 612 in the proximal direction. The slit 618 introduces a point of weakness to each arm 606*a,b*, thereby allowing opposing portions of each arm 606*a,b* at the slots 612 to flex outward as the first axle 404*a* is forced through the minimized section 614 to either receive the first axle 404*a* or remove it from the slots 612.

In some embodiments, the first axle 404*a* may be keyed at or near one or both ends. More specifically, as illustrated, the first axle 404*a* may provide a disassembly feature 620 at each end configured to align with the open-ended slot 612. In the illustrated embodiment, the disassembly features 620 comprise opposing sections of the first axle 404*a* that are reduced in size by providing opposing planar (flat) surfaces, as opposed to a circular cross-section.

The disassembly features 620 may be advantageous in allowing the first axle 404*a* to bypass the minimized section 614 more easily if the disassembly features 620 are oriented with the longitudinal direction of the open-ended slot 612. Accordingly, in some embodiments, before the first axle 404*a* can be removed from the open-ended slot 612, the first axle 404*a* may first be rotated until the disassembly features 620 are aligned with the longitudinal direction of the open-ended slot 612.

Figure 7B:
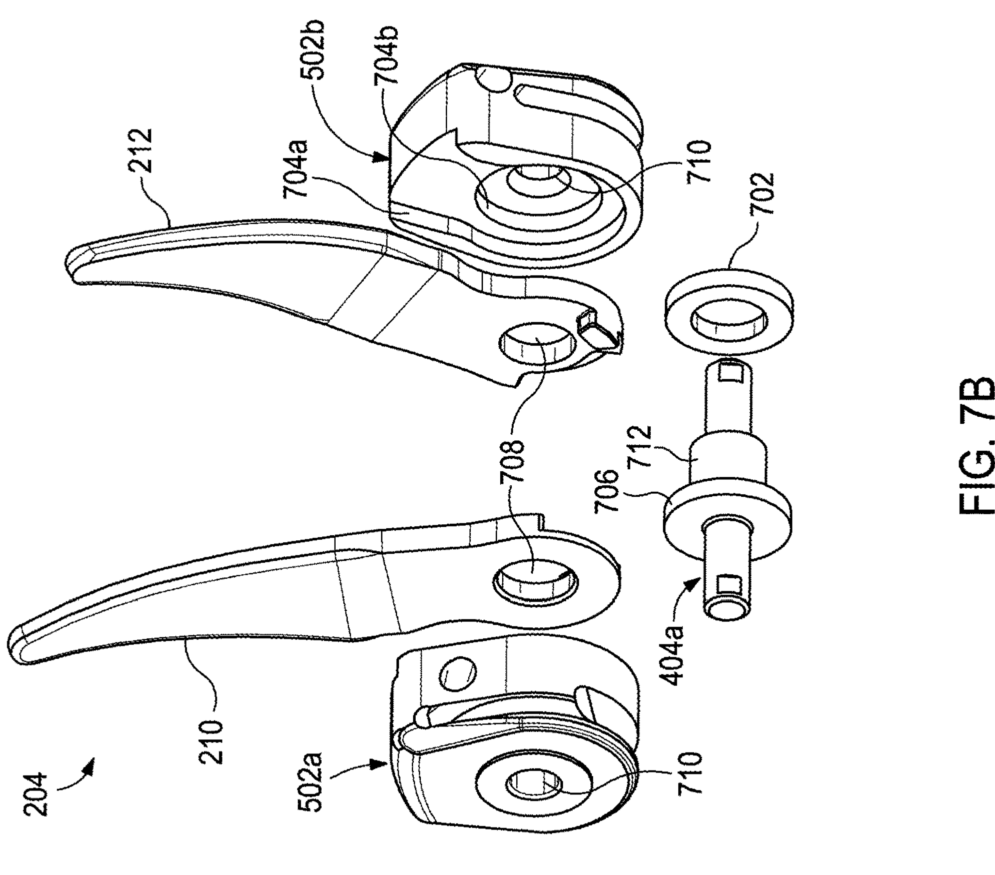
FIGS. 7A and 7B are enlarged exploded left and right isometric views, respectively, of the end effector of FIG. 4, according to one or more embodiments.
Figure 7A:
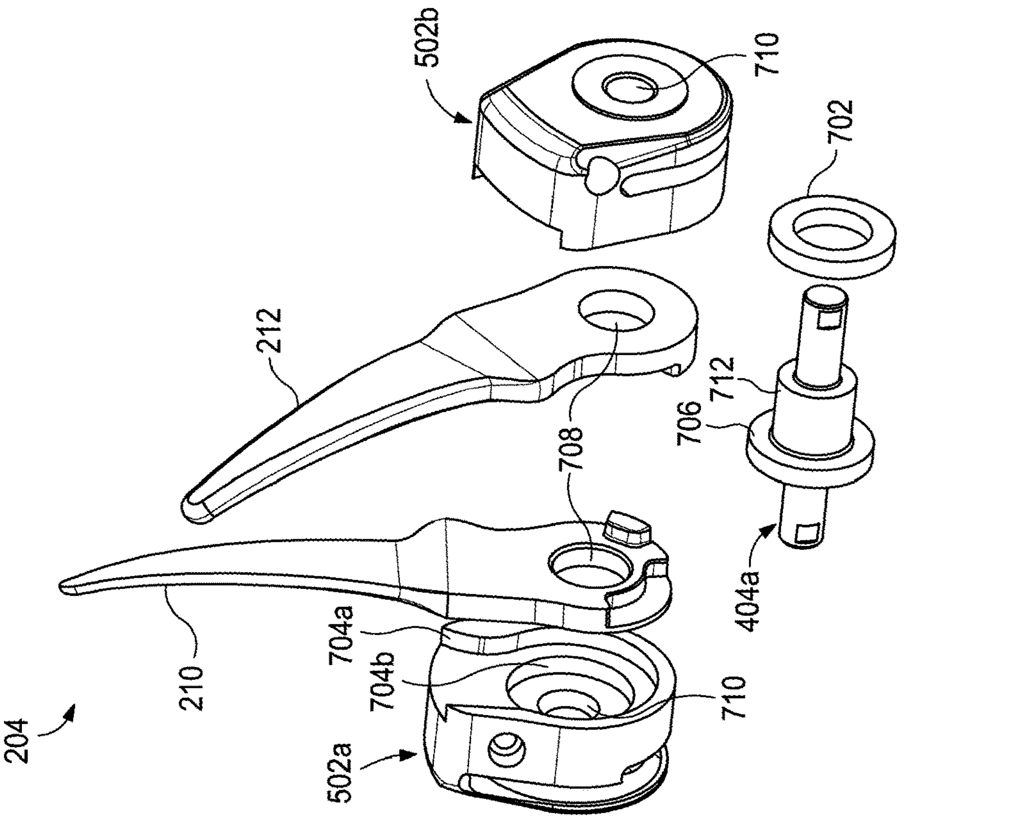

FIGS. 7A and 7B are enlarged exploded left and right isometric views, respectively, of the end effector 204 of FIGS. 5A-5B, according to one or more embodiments. More specifically, FIGS. 7A-7B depict the blades 210, 212 exploded from the corresponding blade holders 502*a,b*, and further depict a washer 702 exploded from the first axle 404*a*.

As illustrated, each blade holder 502*a,b* defines a first recess 704*a* configured to receive and seat the corresponding blade 210, 212 such that movement (rotation) of the blade holder 502*a,b* will correspondingly move (rotate) the corresponding blade 210, 212. Each blade holder 502*a,b* may further define a second recess 704*b* defined within the first recess 704*a* and otherwise deeper into the material of the blade holder 502*a,b*. Each second recess 704*b* may be configured to receive a portion of the first axle 404*a*. More specifically, the second recess 704*b* defined in the first blade holder 502*a* may be configured to receive an enlarged radial shoulder 706 defined on and otherwise forming part of the first axle 404*a*. In contrast, the second recess 704*b* defined in the second blade holder 502*b* may be configured to receive the washer 702. As will be appreciated, the orientation of the first axle 404*a* may be switched such that the enlarged radial shoulder 706 is alternatively received within the second recess 704*b* of the second blade holder 502*b* and the washer 702 is received within the second recess 704*b* of the first blade holder 502*a*, without departing from the scope of the disclosure.

Each blade 210, 212 defines a central aperture 708 coaxially alignable with an axle aperture 710 defined in the corresponding blade holder 502*a,b*. The central and axle apertures 708, 710 are configured to receive portions of the first axle 404*a*. Moreover, in some embodiments, the diameter of the central apertures 708 may be larger than the diameter of the axle apertures 710. This allows the blades 210, 212 to be mounted to the first axle 404*a* at a bushing 712 defined by the first axle 404*a*.

When the blades 210, 212 are properly mounted to the first axle 404*a* at the bushing 712, the enlarged radial shoulder 706 is arranged on one side of the blades 210, 212 and the washer 702 is arranged on the opposing side of the blades 210, 212. With the blades 210, 212 mounted to the first axle 404*a* and pushed up against the enlarged radial shoulder 706, the washer 712 may then be received on the first axle 404*a* and secured (welded) thereto. In at least one embodiment, the washer 702 may be secured to the bushing 712. Securing the washer 702 to the first axle 404*a* axially secures the blades 210, 212 to the first axle 404*a*, but simultaneously allows the blades 210, 212 to rotate relative to one another during operation of the end effector 204.

The end effector 204 includes various high-wear components that can mechanically or physically degrade over time and thereby limit the useful life of the end effector 204. The drive cables 408*a-d* (FIG. 4), for example, can fatigue over time, which can affect the precision and operability of the end effector 204 and surgical tool 200 (FIG. 2). Similarly, the cutting edges of the blades 210, 212 may dull over time, which can also affect the proficiency of the end effector 204. Consequently, the end effector 204 may be designed to be used for only a predetermined number of procedures, and once the predetermined number of procedures is reached, the operator (e.g., a nurse, a doctor, etc.) may be unable to continue using the end effector 204. In such cases, the entire surgical tool 200 would conventionally be discarded, which can have an adverse impact on the environment.

According to embodiments of the present disclosure, instead of discarding the end effector 204, the end effector 204 may be disassembled, and its high-wear components (e.g., the blades 210, 212) can be replaced, following which the end effector 204 may be reassembled and placed back into service. As described herein, the blades 210, 212 may be removed from the remaining portions of the end effector 204 and replaced, as needed, thereby potentially providing the user (e.g., a surgeon, a nurse, etc.) with a new set of blades 210, 212 for every new use of the surgical tool 200 (FIG. 2).

Figure 8:
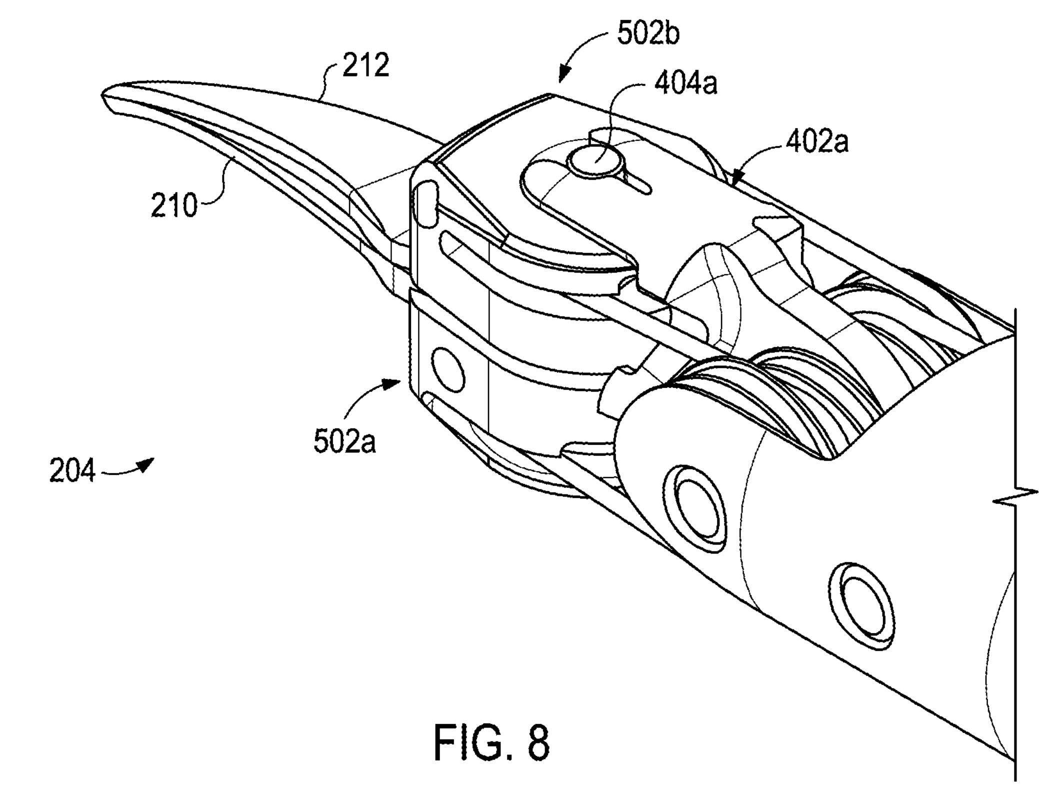
FIGS. 8-11 depict progressive steps of disassembly of the end effector, according to embodiments of the present disclosure.

FIGS. 8-11 depict progressive steps of disassembly of the end effector 204, according to embodiments of the present disclosure. In FIG. 8, the end effector 204 is in an assembled state, where the blades 210, 212 and corresponding blade holders 502*a,b* are rotatably mounted to the distal clevis 402*a* at the first axle 404*a*, as generally described above. The blades 210, 212 are shown in FIG. 8 in the closed position. In some embodiments, prior to commencing the disassembly process of the end effector 204, the drive housing 208 (FIG. 2) of the surgical tool 200 (FIG. 2) may first be detached from the robotic manipulator. As described below, decoupling from the robotic manipulator may allow the drive cables 408*a-d* to payout (e.g., dispense cable length) without being impeded by motor-driven driven drive outputs of the robotic manipulator.

Figure 9:
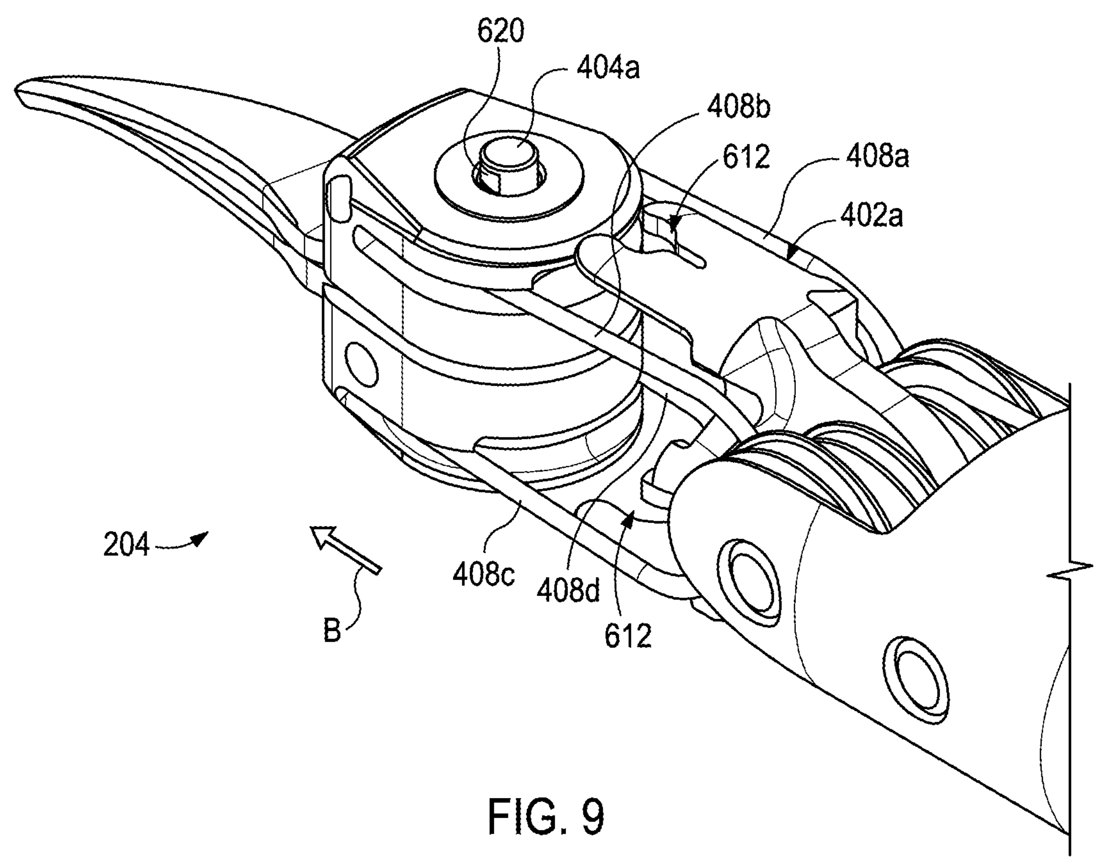

In FIG. 9, the end effector 204 is transitioned from the assembled state to an extended state. More specifically, the end effector 204 is moved distally, as shown by the arrow B, thereby disengaging the first axle 404*a* from the distal clevis 402*a*. In at least one embodiment, this may be done manually by an operator by manually grasping the blade holders 502*a,b* and dislodging the first axle 404*a* from the open-ended slots 612 in the distal direction B. This motion effectively separates the end effector 204 from the distal clevis 402*a*. Disengaging the first axle 404*a* from the distal clevis 402*a* includes forcing the first axle 404*a* out of the open-ended slots 612. In some embodiments, the disassembly features 620 defined at or near each one or both ends of the first axle 404*a* may be first rotated to a "home" orientation where the disassembly features 620 are aligned with the longitudinal direction of the open-ended slots 612.

Once the disassembly features 620 are angularly oriented to the home orientation, the end effector 204 may be manually moved distally B to separate the end effector 204 from the distal clevis 402*a*. In at least one embodiment, it may require a load of at least 11.5 Newtons to force the first axle 404*a* out of the slots 612 and otherwise transition the end effector 204 to the extended state. As will be appreciated, the design and configuration of the slots 612 can be tuned to any desired preload.

To enable the end effector 204 to be pulled distally, the surgical tool 200 (FIG. 2) may provide or otherwise incorporate slack into the design at the drive housing 208 (FIG. 2). More specifically, the drive cables 408*a-d* may each be configured to payout "slack" as the end effector 204 is pulled distally B. In at least one embodiment, this can be accomplished by rotating input capstans arranged within the drive housing 208 and associated with each drive cable 408*a-d*. Rotating the input capstans can be done manually by physically engaging and rotating the input capstans, or could alternatively be done by pulling the end effector 204 distally B. As the input capstans rotate, the drive cables 408*a-d* may be able to unspool or "pay out" cable through various spooling capstan mechanisms.

Figure 10:
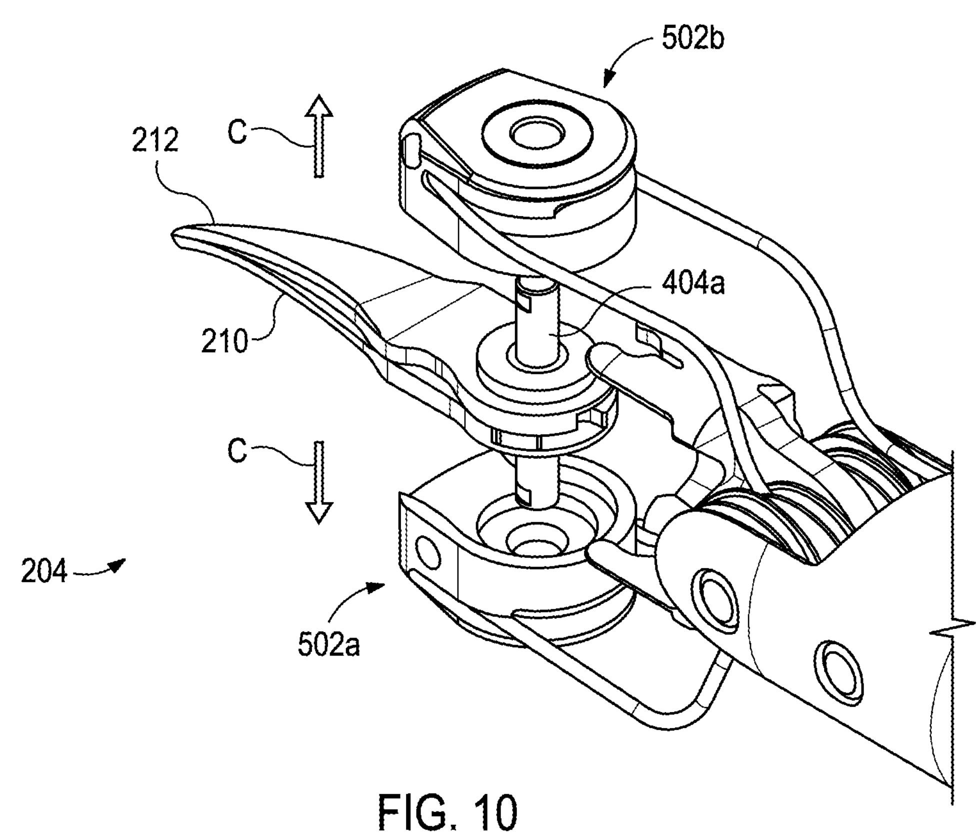

In FIG. 10, once the end effector 204 is moved to the extended state, the blade holders 502*a,b* may then be separated from the blades 210, 212, respectively. More specifically, the blade holders 502*a,b* may be laterally displaced from the blades 210, 212 in opposing lateral directions, as shown by the arrows C. The blade holders 502*a,b* may be laterally displaced C until clear of the first axle 404*a*.

Figure 11:
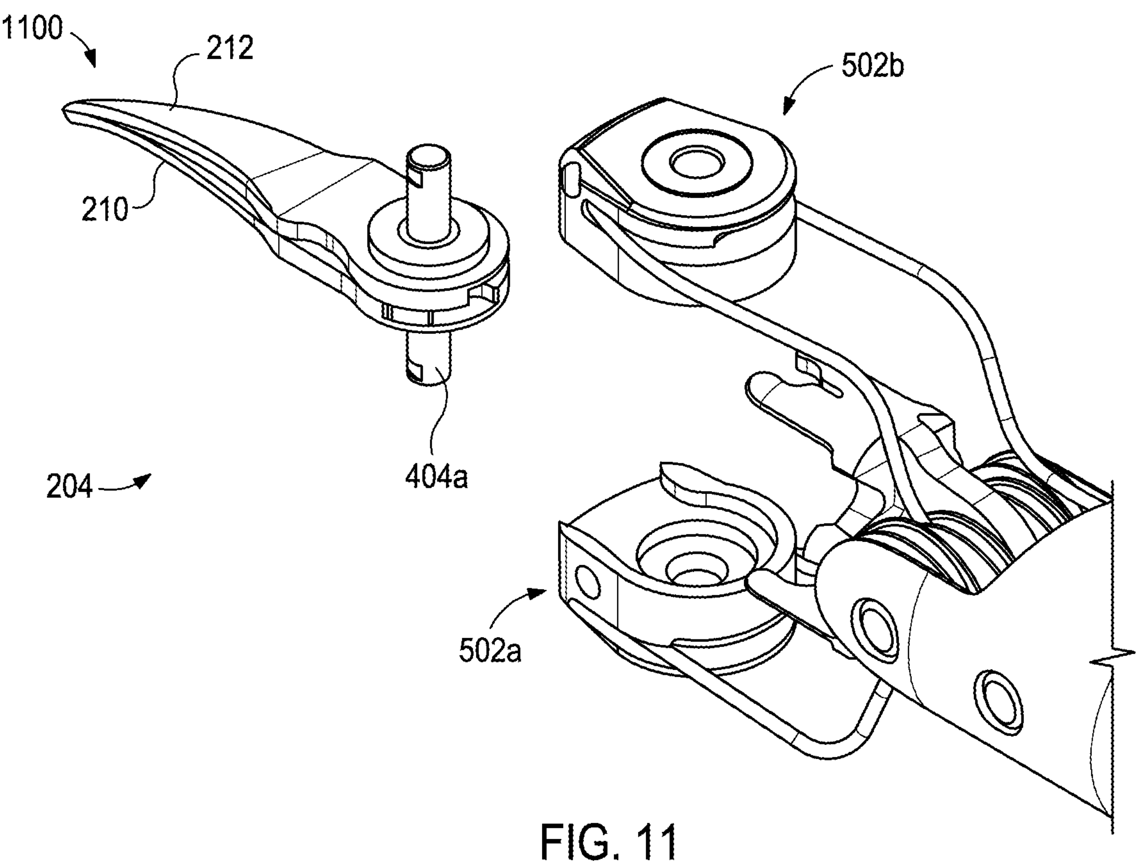

In FIG. 11, once the blade holders 502*a,b* are clear of the first axle 404*a*, the blades 210, 212 and the axle 404*a* may be removed (separated) from the remaining portions of the end effector 204. The separated blades 210, 212 and the axle 404*a* will be cooperatively referred to herein as a "blade set" 1100. The blade set 1100 may then be refurbished or entirely replaced with a new blade set.

Figure 12:
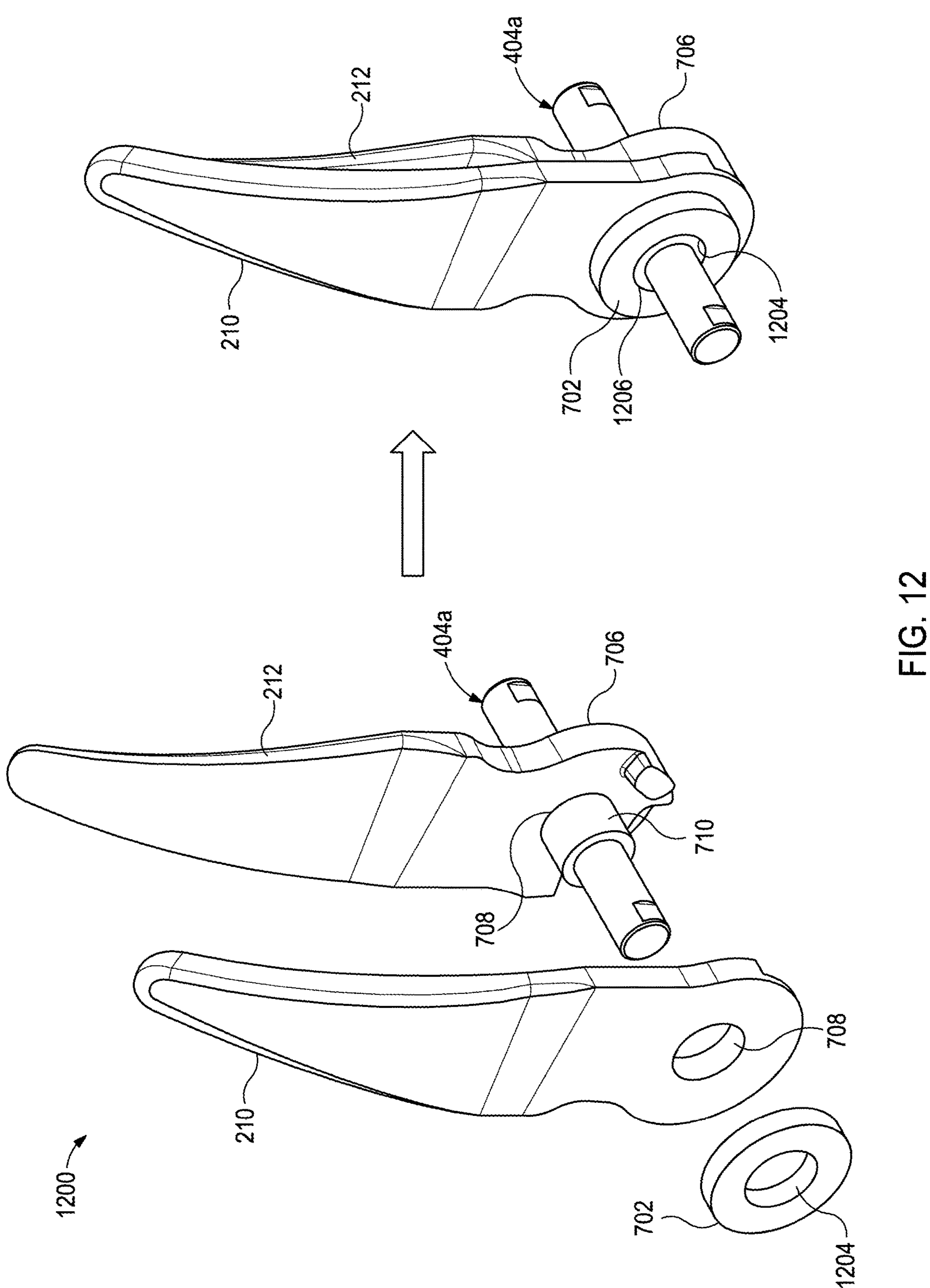
FIG. 12 is an enlarged isometric view of reassembling a new blade set, according to one or more embodiments of the disclosure.

FIG. 12 is an enlarged isometric view of assembling a new blade set 1200, according to one or more embodiments of the disclosure. As illustrated, the blade set 1200 includes the first and second blades 210, 212, the first axle 404*a*, and the washer 702. In some embodiments, the blade set 1200 may be the same blade set used in the end effector 204 (FIGS. 8-11) prior to disassembly. In such embodiments, and prior to reassembly, the blades 210, 212 may have been refurbished and/or re-sharpened. In other embodiments, however, the blade set 1200 may comprise an entirely or partially new blade set, without departing from the scope of the disclosure.

To assemble the blade set 1200, the blades 210, 212 may first be mounted to the first axle 404*a* at the bushing 710. More particularly, the bushing 710 may be received within the central apertures 708 of each blade 210, 212 and the second blade 212 may be pushed up against the enlarged radial shoulder 706 (mostly occluded). The washer 702 may then be mounted to the first axle 404*a* and pushed against the first blade 210 opposite the enlarged radial shoulder 706. As illustrated, the washer 702 includes a central aperture 1204 sized to receive the first axle 404*a*. In some embodiments, as illustrated, central aperture 1204 may be sized to receive the bushing 710. Once placed against the first blade 210, the washer 702 may be secured to the first axle 404*a*, such as being welded to the first axle 404*a* at an interface 1204 between the bushing 710 and the central aperture 1204.

The new or refurbished blade set 1200 is assembled, foregoing steps of disassembly and detachment of the end effector 204 up to this point may then be reversed to place the surgical tool 200 (FIG. 2) back into service. In particular, in a process that reverses the processes outlined in FIGS. 10 and 11 above, the blade holders 502*a,b* may be mounted to the first axle 404*a* on opposing sides of the blade set 1200.

In a process that reverses the process outlined in FIG. 9, the end effector 204 may then be transitioned back to the assembled state. To accomplish this, the first axle 404*a* is aligned with the open-ended slots 612 of the distal clevis 402*a*, and the end effector 204 is moved proximally to receive the opposing ends of the first axle 404*a* in the slots 612. In some embodiments, the disassembly features 620 defined at or near each end of the first axle 404*a* may be first rotated to the home orientation where the disassembly features 620 are aligned with the longitudinal direction of the open-ended slots 612. The slack in the drive cables 408*a-d* may then be taken up at the drive housing 208 (FIG. 2).

Figures 13A, 13B:
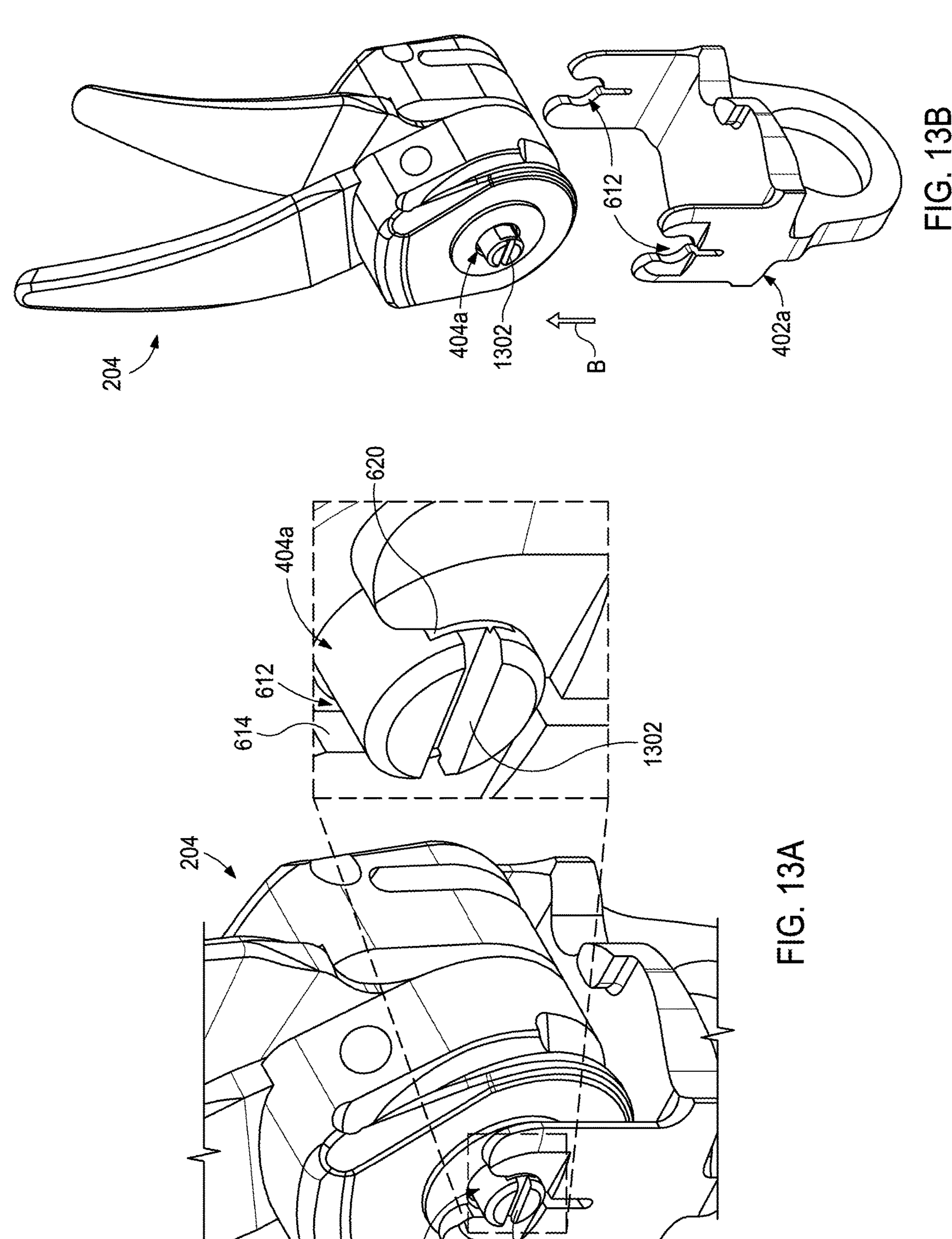
FIGS. 13A and 13B are enlarged isometric and exploded views, respectively, of the end effector, according to one or more additional embodiments of the present disclosure.

FIGS. 13A and 13B are enlarged isometric and exploded views, respectively, of the end effector 204, according to one or more additional embodiments of the present disclosure. As generally described above, the disassembly feature 620 may be defined at or near one or both ends of the first axle 404*a*. In the illustrated embodiment, the disassembly feature 620 comprises opposing sections of the first axle 404*a* that are reduced in size by providing opposing planar (flat) surfaces, as opposed to a circular cross-section.

The first axle 404*a* is able to more easily bypass the minimized section 614 of the open-ended slot 612 when the disassembly features 620 are oriented with the longitudinal direction of the open-ended slot 612. In the illustrated embodiment, aligning the disassembly feature 620 with the longitudinal direction of the open-ended slot 612 may achieved by engaging and manipulating one or more external keys 1302 defined on one or both of the ends of the first axle 404*a*. In at least one embodiment, the external keys 1302 may comprise a channel or slit defined in the end face of the first axle 404*a*. In such embodiments, an operator may be able to insert a flat-headed tool, such as a flat head screwdriver (not shown), and manually rotate the first axle 404*a* to the proper angular orientation.

In FIG. 13B, the end effector 204 is transitioned from the assembled state to an extended state, where the end effector 204 is moved distally, as shown by the arrow B, thereby disengaging the first axle 404*a* from the distal clevis 402*a*. Disengaging the first axle 404*a* from the distal clevis 402*a* includes forcing the first axle 404*a* out of the open-ended slots 612. Prior to disengaging the first axle 404*a* from the distal clevis 402*a*, the operator may manually engage the external keys 1302 and rotate the first axle 404*a* until the disassembly features 620 are rotated to the "home" orientation where the disassembly features 620 are aligned with the longitudinal direction of the open-ended slots 612. Once the disassembly features 620 are angularly oriented to the home orientation, the end effector 204 may be manually moved distally B to separate the end effector 204 from the distal clevis 402*a*.

Figure 14B:
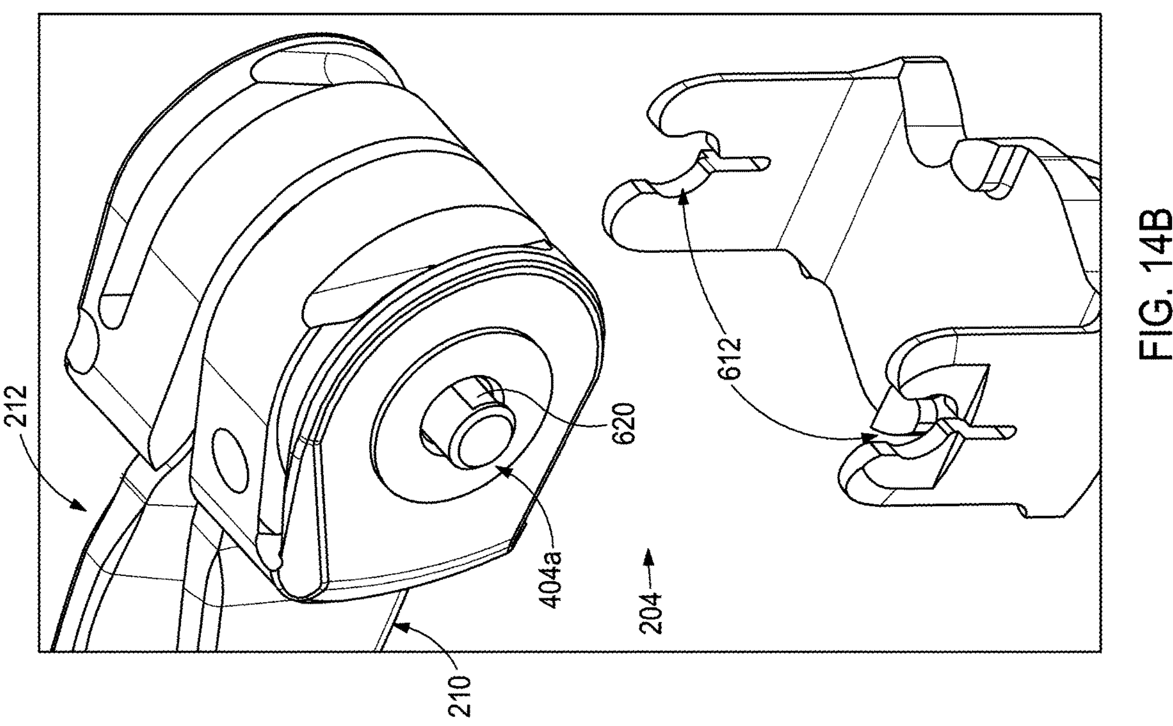
FIGS. 14A and 14B are enlarged isometric and exploded views, respectively, of the end effector, according to one or more additional embodiments of the present disclosure.
Figure 14A:
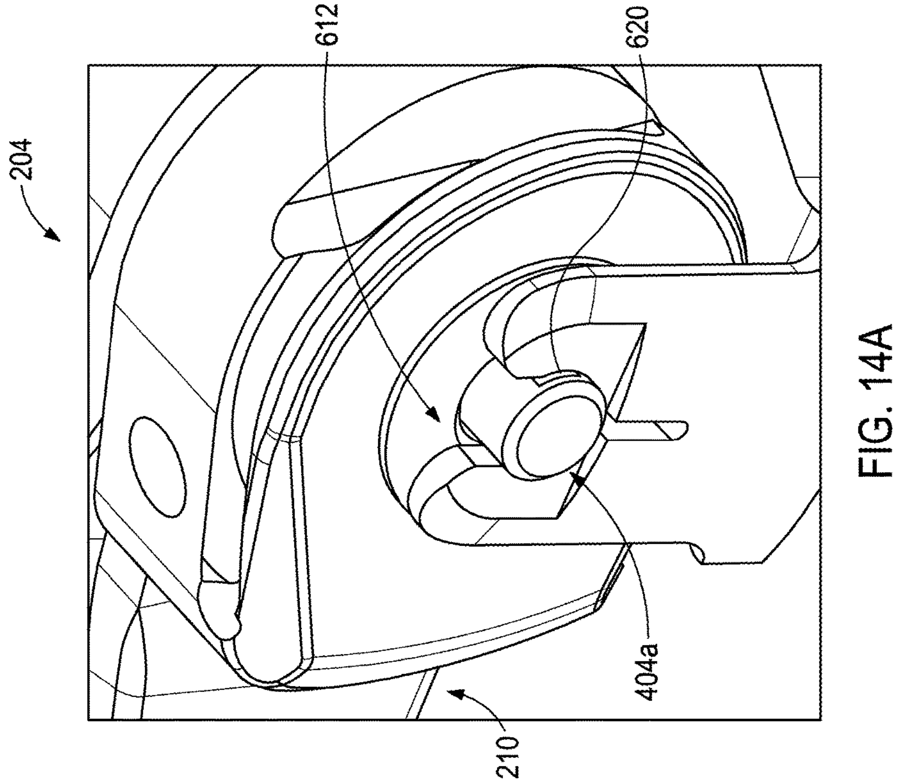

FIGS. 14A and 14B are enlarged isometric and exploded views, respectively, of the end effector 204, according to one or more additional embodiments of the present disclosure. In some embodiments, the first axle 404*a* may be operatively coupled to and otherwise form an integral part of one of the blades 210, 212. In the illustrated embodiment, the first axle 404*a* forms an integral part of the first jaw 210. In such embodiments, rotation of the first jaw 210 will correspondingly rotate the first axle 404 in the same angular direction.

In the illustrated embodiment, the disassembly features 620 are defined on the one or both ends of the first axle 404*a* such that the disassembly features 620 align with the longitudinal direction of the open-ended slots 612 at an angular orientation that is outside of the normal operating range of the end effector 204. In the illustrated embodiment, for example, the first jaw 210 must be rotated approximately perpendicular to the longitudinal direction of the open-ended slot 612, thereby aligning the disassembly feature 620 with said longitudinal direction. In such embodiments, the jaws 210, 212 may be designed to never reach perpendicular to the longitudinal direction of the open-ended slots 612 during operation. This assures that it is not possible to remove the first axle 404*a* from the open-ended slots 612 in any other angular position.

In FIG. 14B, the end effector 204 is transitioned from the assembled state to an extended state, where the end effector 204 is moved distally, as shown by the arrow B, and thereby disengaging the first axle 404*a* from the distal clevis 402*a*. As indicated, the jaw 210 must first be rotated until the disassembly features 620 angularly align with the longitudinal direction of the open-ended slots 612. Disengaging the first axle 404*a* from the distal clevis 402*a* then includes forcing the first axle 404*a* out of the open-ended slots 612.

Embodiments disclosed herein include:

A. A method of replacing blades of an end effector of a surgical tool includes moving the end effector distally from an assembled state, where the end effector is rotatably mounted to a clevis of a wrist of the surgical tool, to an extended state, where an axle of the end effector is dislodged from open-ended slots defined in opposing first and second arms of the clevis, the end effector including opposing first and second blades, and first and second blade holders rotatably mounted to the axle, the first blade being mounted to the first blade holder, and the second blade being mounted to the second blade holder. The method further includes separating the first and second blade holders from the first and second blades in opposing lateral directions until the first and second blade holders are removed from the axle, removing the first and second blades and the axle from remaining portions of the end effector, assembling a new blade set comprising first and second new blades and a new axle, mounting the first and second blade holders to the new axle and thereby mounting the first and second new blades to the first and second blade holders, respectively, and moving the end effector proximally and back to the assembled state by receiving the new axle within the open-ended slots.

B. A surgical tool that includes a drive housing, an elongate shaft extending distally from the drive housing, a wrist arranged at a distal end of the shaft and including a clevis providing a main body and opposing first and second arms extending distally from the main body, and an open-ended slot defined in each arm and open in a distal direction. The surgical tool further including an end effector operatively coupled to the wrist and including an axle mounted to the clevis at each open-ended slot, each end of the axle providing a disassembly feature alignable with a longitudinal direction of each open-ended slot, and opposing first and second blades rotatably mounted to the axle.

C. An end effector for a surgical tool that includes a clevis providing a main body and opposing first and second arms extending distally from the main body, an open-ended slot defined in each arm and open in a distal direction, each open-ended slot defining a minimized section that leads into an enlarged section, the minimized section providing a smaller gap as compared to the enlarged section, an axle mounted to the clevis at each open-ended slot, first and second blade holders rotatably mounted to the axle, a first blade mounted to the first blade holder, and a second blade mounted to the second blade holder, wherein the first and second blade holders and the first and second blades are separable from the clevis by forcing the axle out of the open-ended slot of each arm in the distal direction.

Each of embodiments A, B, and C may have one or more of the following additional elements in any combination: Element 1: wherein moving the end effector distally from the assembled state to the extended state comprises manually grasping the end effector and dislodging the axle from the open-ended slots in a distal direction. Element 2: wherein each open-ended slot defines a minimized section that leads into an enlarged section, the minimized section providing a smaller gap as compared to the enlarged section, and wherein moving the end effector distally from the assembled state to the extended state further comprises forcing the axle through the minimized section and out of the open-ended slots. Element 3: wherein the axle provides opposing planar surfaces at each end and forcing the axle through the minimized section is preceded by aligning the opposing planar surfaces with a longitudinal direction of each open-ended slot. Element 4: wherein each end of the axle provides a disassembly feature and wherein moving the end effector distally from the assembled state to the extended state is preceded by rotating the axle to a home orientation where the disassembly features are aligned with a longitudinal direction of the open-ended slots. Element 5: wherein a plurality of drive cables extend from a drive housing of the surgical tool and terminate at the first and second blade holders, and wherein moving the end effector distally from the assembled state to the extended state comprises paying out slack in the plurality of drive cables from the drive housing as the end effector moves distally. Element 6: wherein separating the first and second blade holders from the first and second blades in opposing lateral directions comprises maintaining the plurality of drive cables attached to the blade holders as the first and second blade holders are removed from the axle. Element 7: wherein assembling the new blade set comprises receiving the new axle within central apertures defined in each of the new blades, advancing the first and second blades along the new axle until a first side of the first and second new blades engages an enlarged radial shoulder defined by the new axle, mounting a washer on the axle and engaging a second side of the first and second blades with the washer, and securing the washer to the new axle. Element 8: wherein moving the end effector distally from the assembled state to the extended state is preceded by decoupling a drive housing of the surgical tool from a robotic manipulator.

Element 9: wherein each open-ended slot defines a minimized section that leads into an enlarged section, the minimized section providing a smaller gap as compared to the enlarged section. Element 10: wherein the disassembly feature comprises opposing planar surfaces alignable with the longitudinal direction of each open-ended slot to force the axle out of the open-ended slot. Element 11: further comprising a longitudinal slit defined in each arm and extending contiguous with and from a corresponding open-ended slot in a proximal direction, and wherein the longitudinal slit allows opposing portions of each arm the corresponding open-ended slot to flex outward as the axle is forced out of the corresponding open-ended slot. Element 12: wherein the end effector is separable from the clevis by forcing the axle out of the open-ended slot of each arm in the distal direction. Element 13: further comprising first and second blade holders rotatably mounted to the axle, the first blade being mounted to the first blade holder, and the second blade being mounted to the second blade holder, and a plurality of drive cables extending from the drive housing and terminating at the first and second blade holders, wherein the end effector is separable from the clevis by forcing the axle out of the open-ended slot of each arm in the distal direction, and wherein the first and second blades are separable from the first and second blade holders, respectively, while the plurality of drive cables remain attached to the first and second blade holders. Element 14: wherein the first blade holder defines a first pulley configured to receive first and second drive cables of the plurality of drive cables, and the second blade holder defines a second pulley configured to receive third and fourth drive cables of the plurality of drive cables. Element 15: wherein axle includes an enlarged radial shoulder and the first and second blades are secured to the axle between the enlarged radial shoulder on a first side and a washer is fixed to the axle on a second side.

Element 16: wherein each end of the axle provides a disassembly feature comprising opposing planar surfaces alignable with a longitudinal direction of each open-ended slot to force the axle out of the open-ended slot. Element 17: further comprising a washer mountable to the axle, wherein the first and second blades are secured to the axle between the enlarged radial shoulder on a first side and the washer on a second side.

By way of non-limiting example, exemplary combinations applicable to A, B, and C include: Element 1 with Element 2; Element 2 with Element 3; Element 5 with Element 6; Element 9 with Element 10; Element 10 with Element 11; and Element 13 with Element 14.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method of replacing blades of an end effector of a surgical tool, comprising:

moving the end effector distally from an assembled state, where the end effector is rotatably mounted to a clevis of a wrist of the surgical tool, to an extended state, where an axle of the end effector is dislodged from open-ended slots defined in opposing first and second arms of the clevis, the end effector including:

opposing first and second blades; and first and second blade holders rotatably mounted to the axle, the first blade being mounted to the first blade holder, and the second blade being mounted to the second blade holder;

separating the first and second blade holders from the first and second blades in opposing lateral directions until the first and second blade holders are removed from the axle;

removing the first and second blades and the axle from remaining portions of the end effector;

assembling a new blade set comprising first and second new blades and a new axle;

mounting the first and second blade holders to the new axle and thereby mounting the first and second new blades to the first and second blade holders, respectively; and moving the end effector proximally and back to the assembled state by receiving the new axle within the open-ended slots.

2. The method of claim 1, wherein moving the end effector distally from the assembled state to the extended state comprises manually grasping the end effector and dislodging the axle from the open-ended slots in a distal direction.

3. The method of claim 2, wherein each open-ended slot defines a minimized section that leads into an enlarged section, the minimized section providing a smaller gap as compared to the enlarged section, and wherein moving the end effector distally from the assembled state to the extended state further comprises forcing the axle through the minimized section and out of the open-ended slots.

4. The method of claim 3, wherein the axle provides opposing planar surfaces at each end and forcing the axle through the minimized section is preceded by aligning the opposing planar surfaces with a longitudinal direction of each open-ended slot.

5. The method of claim 1, wherein each end of the axle provides a disassembly feature and wherein moving the end effector distally from the assembled state to the extended state is preceded by rotating the axle to a home orientation where the disassembly features are aligned with a longitudinal direction of the open-ended slots.

6. The method of claim 1, wherein a plurality of drive cables extend from a drive housing of the surgical tool and terminate at the first and second blade holders, and wherein moving the end effector distally from the assembled state to the extended state comprises paying out slack in the plurality of drive cables from the drive housing as the end effector moves distally.

7. The method of claim 6, wherein separating the first and second blade holders from the first and second blades in opposing lateral directions comprises maintaining the plurality of drive cables attached to the first and second blade holders as the first and second blade holders are removed from the axle.

8. The method of claim 1, wherein assembling the new blade set comprises:

receiving the new axle within central apertures defined in each of the new blades;

advancing the first and second new blades along the new axle until a first side of the first and second new blades engages an enlarged radial shoulder defined by the new axle;

mounting a washer on the new axle and engaging a second side of the first and second new blades with the washer; and securing the washer to the new axle.

9. The method of claim 1, wherein moving the end effector distally from the assembled state to the extended state is preceded by decoupling a drive housing of the surgical tool from a robotic manipulator.

* * * * *